United States Patent
Harish Gopala Pillai

(10) Patent No.: US 12,123,762 B1
(45) Date of Patent: Oct. 22, 2024

(54) SMART MAT THAT SENSES BODY WEIGHT AND RELATED DATA AND TRANSMITS WIRELESSLY TO A PHONE OR HUB

(71) Applicant: Raman Nair Harish Gopala Pillai, Portland, OR (US)

(72) Inventor: Raman Nair Harish Gopala Pillai, Portland, OR (US)

(73) Assignee: THINGS OF A FEATHER LLC, Beaverton, OR (US)

( * ) Notice: Subject to any disclaimer, the term of this patent is extended or adjusted under 35 U.S.C. 154(b) by 543 days.

(21) Appl. No.: 17/463,127

(22) Filed: Aug. 31, 2021

Related U.S. Application Data

(60) Provisional application No. 63/091,188, filed on Oct. 13, 2020.

(51) Int. Cl.
  *G01G 19/44* (2006.01)
  *A61B 5/00* (2006.01)
  (Continued)

(52) U.S. Cl.
  CPC ........... *G01G 19/44* (2013.01); *A61B 5/0205* (2013.01); *A61B 5/6892* (2013.01); *G01G 3/142* (2013.01);
  (Continued)

(58) Field of Classification Search
  CPC ........ G01G 19/44; G01G 3/142; A61B 5/025; A61B 5/6892; A61B 5/02438;
  (Continued)

(56) References Cited

U.S. PATENT DOCUMENTS

| | | | |
|---|---|---|---|
| 8,109,874 B2 * | 2/2012 | Kong | A61B 5/7435 |
| | | | 128/920 |
| 8,696,569 B2 * | 4/2014 | Yuen | A61B 5/02007 |
| | | | 128/920 |

(Continued)

FOREIGN PATENT DOCUMENTS

| | | | | |
|---|---|---|---|---|
| KR | 101644276 | * | 8/2016 | ............. A47C 31/00 |
| WO | WO-2021225270 A1 | * | 11/2021 | ........... G08B 25/016 |

(Continued)

*Primary Examiner* — Jacques M Saint Surin
(74) *Attorney, Agent, or Firm* — Plager Schack LLP; Mark H. Plager; Stephen Hallberg

(57) ABSTRACT

A smart mat and scale to detect and communicate body weight of a user and other related data and a smart mat weight detection, calculation, and communication system configured to wirelessly communicate with nearby devices and over a network to a cloud application service and cloud database are disclosed smart mat (bathroom mat, shower mat, kitchen mat, work area mat, or other household mat or commonly used mat), that has circuitry to inconspicuously sense body weight and related data, transmit wirelessly to a phone or hub is disclosed. The smart mat presented herein incorporates technology to well-known household product and enables gathering of body weight data subconsciously and hence allowing gathering consistent data over period of time. It is also preferred to be flexible, light weight and withstand conventional cleaning practices.

9 Claims, 7 Drawing Sheets

(51) Int. Cl.
*A61B 5/0205* (2006.01)
*A61B 5/024* (2006.01)
*A61B 5/0537* (2021.01)
*G01G 3/142* (2006.01)
*H04L 67/10* (2022.01)
*H04W 88/04* (2009.01)
*H04W 88/16* (2009.01)

(52) U.S. Cl.
CPC .......... *H04L 67/10* (2013.01); *A61B 5/02438* (2013.01); *A61B 5/0537* (2013.01); *H04W 88/04* (2013.01); *H04W 88/16* (2013.01)

(58) Field of Classification Search
CPC ...... A61B 5/0537; H04L 67/10; H04W 88/04; H04W 88/16

USPC ...................................................... 177/25.13
See application file for complete search history.

(56) References Cited

U.S. PATENT DOCUMENTS

| 8,746,086 | B1 * | 6/2014 | Niemeyer | G01L 1/2243 |
| | | | | 73/862 |
| 9,173,576 | B2 * | 11/2015 | Yuen | A61B 5/0059 |
| 9,892,379 | B1 * | 2/2018 | Danyluk | G08B 29/188 |
| 2019/0130727 | A1 * | 5/2019 | Wu | G08B 21/02 |

FOREIGN PATENT DOCUMENTS

| WO | WO-2021225271 A1 * | 11/2021 | ........... A47C 31/123 |
| WO | WO-2023052840 A2 * | 4/2023 | ............. G01G 19/44 |

* cited by examiner

SMART MAT THAT SENSES BODY WEIGHT AND RELATED DATA AND TRANSMITS WIRELESSLY TO A PHONE OR HUB

CLAIM OF BENEFIT TO PRIOR APPLICATION

This application claims benefit to United States Provisional Patent Application 63/091,188, entitled "A SMART MAT THAT SENSES BODY WEIGHT AND RELATED DATA AND TRANSMITS WIRELESSLY TO A PHONE OR HUB," filed Oct. 13, 2020. The United States Provisional Patent Application 63/091,188 is incorporated herein by reference.

BACKGROUND

Embodiments of the invention described in this specification relate generally to devices and systems for general well-being, fitness, and smart home products, and more particularly, to a smart mat (bathroom mat, shower mat, door mat, kitchen mat, or another other type of common household mat or other mat where humans are active, etc.) to detect and communicate body weight and related data.

Devices that gather biometric data on a daily basis is widespread. Most of them require user to wear them or require usage for a specific purpose like exercising, bicycling etc. Many of them fall under the broad category of "wearables". One of the drawbacks of such devices is the need for user to take conscious action by actually wearing and/or removing the device.

A conventional bathroom scale, for example, requires a conscious and affirmative user action by stepping on it. Technology has been added to weight scales, better known as "smart weighing scales" that record body weight and send data wirelessly.

Existing solutions require conscious user interaction to achieve goal of monitoring weight. Also, existing mats specifically designed to measure body pressure have existed for while. These are dedicated for purpose of biomedical diagnosis. Examples include products like MatScan from Tekscan, and other such existing options with similar applications by way of a dedicated device and primarily for biometric purpose. Similarly, weight and pressure sensing devices have been incorporated into shoes in some cases.

Conventional bathroom scales (or "weighing scales") are heavy. Conventional weighing scales typically include four strain gauges in a Wheatstone bridge configuration with a heavy glass platform to hold body weight. Also, the distance between two gauges determines thickness of glass. The heavy glass platform is typically a thick tempered glass platform which, for load bearing reasons, typically weighs in excess of two pounds (lbs).

Therefore, what is needed is a way to use any commonly used material as a shower, bath, and/or household mat without impeding the reliability of body weight measurement, and to routinely collect data on body weight measurements, and provide offline processing to infer significant biometric and control data, but which is much lighter in weight than conventional bathroom scales so as to provide easier handling as a household mat/scale which people (or "users") are willing to adopt for routine use (e.g., daily use, weekly use, etc.).

BRIEF DESCRIPTION

A smart mat and platform scale to detect, measure, and communicate body weight of a user and other related data and a smart mat weight detection, calculation, and communication system configured to measure weight of a user and wirelessly transmit weight data to a host are disclosed. In some embodiments, the smart mat and platform scale (hereinafter also referred to as "smart mat-scale" or "smart mat-scale platform") is made of a flexible, light weight, and cleanable material, and includes circuitry to automatically and inconspicuously sense body weight and other related data of a user when the user steps or stands on the smart mat-scale platform. In some embodiments, the smart mat-scale transmits the body weight and other related data for review and storage after each instance of the user stepping onto or standing on the platform and the smart mat-scale detecting the body weight and other related information about the user. In some embodiments, the smart mat-scale detects body weight and other related information about the user automatically and inconspicuously communicates the detected body weight and other related data for review and storage. In some embodiments, the smart mat-scale communicates the detected body weight and other related data for review and storage by transmitting the body weight and other related data wirelessly to a host for data processing and for persistently storing the data in storage devices.

In some embodiments, the smart mat-scale is configured for daily use as a household mat. Examples of household mats for which the smart mat-scale would be suitably configured for daily use include, without limitation, bathroom mats, shower mats, door mats, kitchen mats, entryway mats, garage mats, other types of common household mats, or any other kind of mats used in locations where humans are active (hereinafter referred to individually as a "household mat" and collectively as "household mats"). In this way, a user going about usual daily activities may unconsciously step on the smart mat-scale as would be normal for a household mat during routine, day-to-day activities, such as washing hands at a sink, taking a shower, etc. However, unlike a usual household mat, the smart mat-scale is configured to capture body weight and other related data about the user when the user steps upon or stands on the smart mat-scale. Furthermore, the smart mat-scale is configured to capture body weight and other related data about the user whether or not the user consciously intends, when the user steps onto and/or stands on the smart mat-scale, for the smart mat-scale to capture body weight and other related data. As such, the smart mat-scale captures the body weight and other related data even when the user is going about daily activities and is unconsciously, unknowingly, or mindlessly stepping upon or standing on the smart mat-scale.

In some embodiments, the data processing and storage devices to which the smart mat-scale wirelessly transmits the body weight and other related data comprise at least a smartphone of the user and a home-based data hub. In some embodiments, the smartphone includes a mobile app and the home-based hub includes an application for aggregating the routine, day-to-day body weight and other related data for reporting and tracking body weight and other related data trends of the user over time. Based on historical data, the mobile app or home based hub can automatically associate weight or other related information to specific individuals using the smart mat-scale. Such information could be used to determine security of home or work space. For example, when the smart mat-scale is a household entryway mat and is placed at a door step, unrecognized weight measurements or other unrecognized information could trigger an alert system.

In some embodiments, the smart mat-scale is a small form smart mat-scale that utilizes a distributed weighing scheme and is configured for daily use as a smart scale to measure body weight. The small form smart mat-scale of some embodiments comprises a small subset of Wheatstone bridge circuits, each having strain gauge circuitry. In some embodiments, the strain gauge circuitry of the small subset of Wheatstone bridge circuits are placed adjacent to each other, resulting in a lighter weighing and less thick platform than conventional weighing scales. In some embodiments, the small form smart mat-scale utilizes a plurality of Wheatstone bridge circuits, each with its own set of strain gauge circuitry. As a result, the weight and thickness of a glass platform can be reduced to less than half of the weight and thickness of the heavy glass platforms of conventional weighing scales.

In addition to measuring body weight, the small form smart mat-scale further comprises additional circuitry that is configured to measure body mass index (BMI) using bioelectrical impedance analysis and heart rate measurement in connection with the user's mobile device smartphone or the data hub.

In some embodiments, the small form smart mat-scale is configured to allow for measurement of other useful data, such as weight spread between heel and toe in a normal standing posture. The data could be used to determine gait issues such as bad posture or structural deficiencies in the feet. In some embodiments, the small form smart mat-scale is configured to also measure transfer of weight from one foot to another, such as may occur while training to improve a user's golf swing or baseball bat swing.

In some embodiments, the small form smart mat-scale comprises a single slab platform that encompasses all four pressure sensor tiles and the corresponding four embedded Wheatstone bridge circuits. In some embodiments, the small form smart mat-scale comprises a plurality of foldable platform slabs which allows the small form smart mat-scale to be folded and unfolded for use as a foldable smart scale. In some embodiments, the plurality of foldable platform slabs comprises two foldable platform slabs. In some embodiments, the plurality of foldable platform slabs comprises four foldable platform slabs.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having thus described the invention in general terms, reference is now made to the accompanying drawings, which are not necessarily drawn to scale, and which show different views of different example embodiments.

Figure 1:
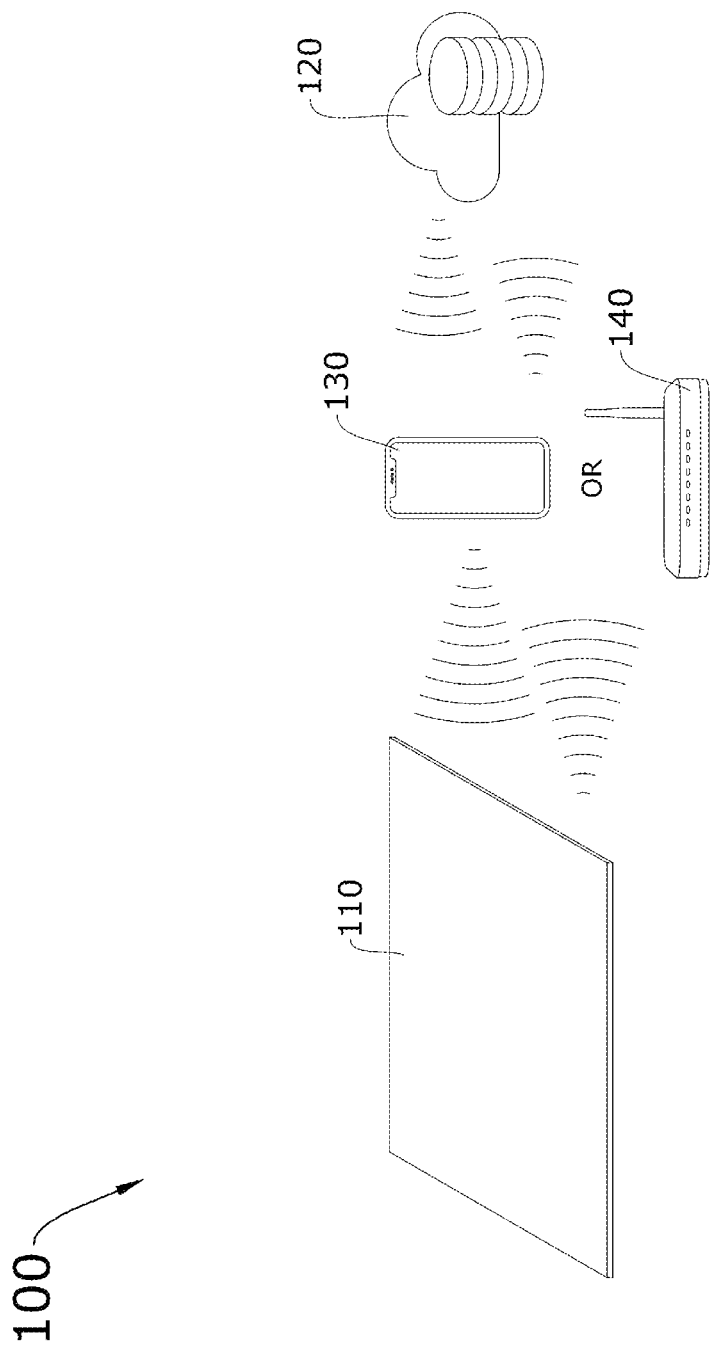

FIG. 1 conceptually illustrates a smart mat weight detection, calculation, and communication system configured to measure weight of a user and wirelessly transmit weight data to at least one of a local host device and an external network-accessible cloud server host that provides a cloud application service and cloud database.

Figure 2:
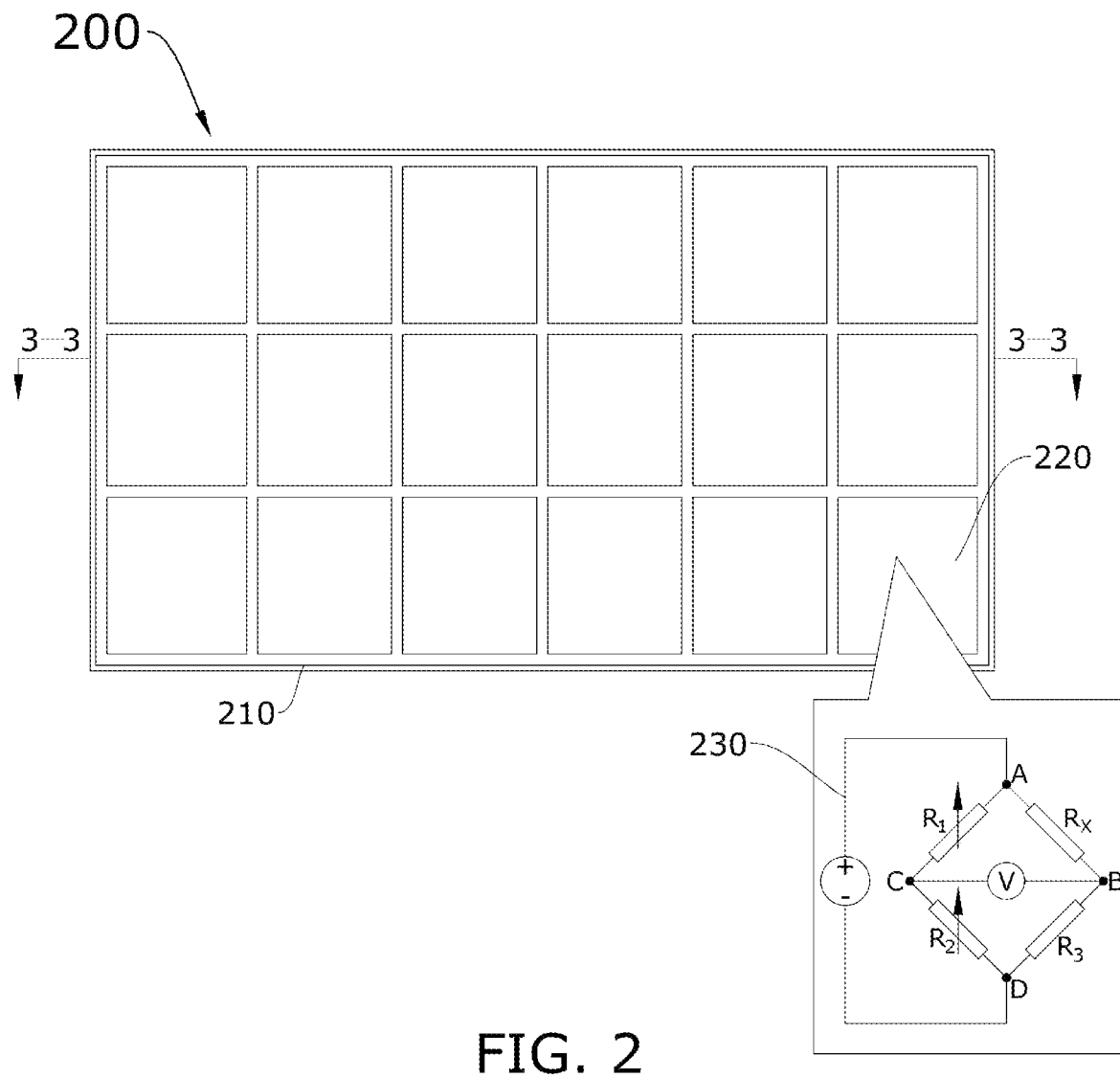

FIG. 2 conceptually illustrates a top view of a smart mat-scale in some embodiments.

Figure 3:
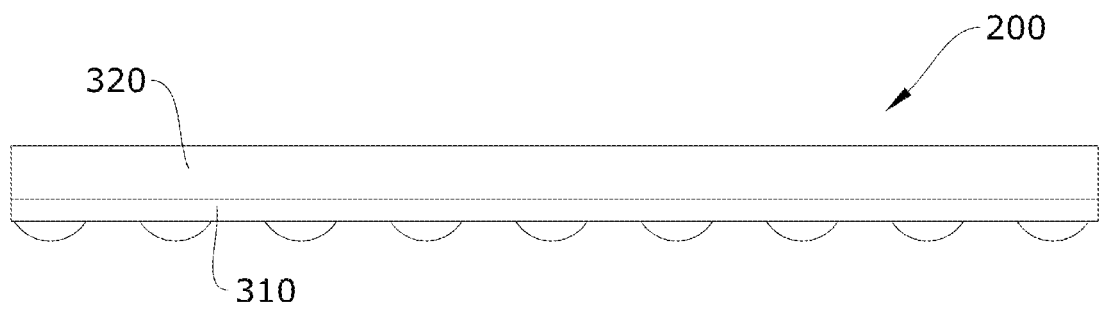

FIG. 3 conceptually illustrates a front view taken along line 3-3 of the smart mat-scale in FIG. 2 demonstrating a conventional textile fabric platform that is a used primarily for cleaning feet.

Figure 4:
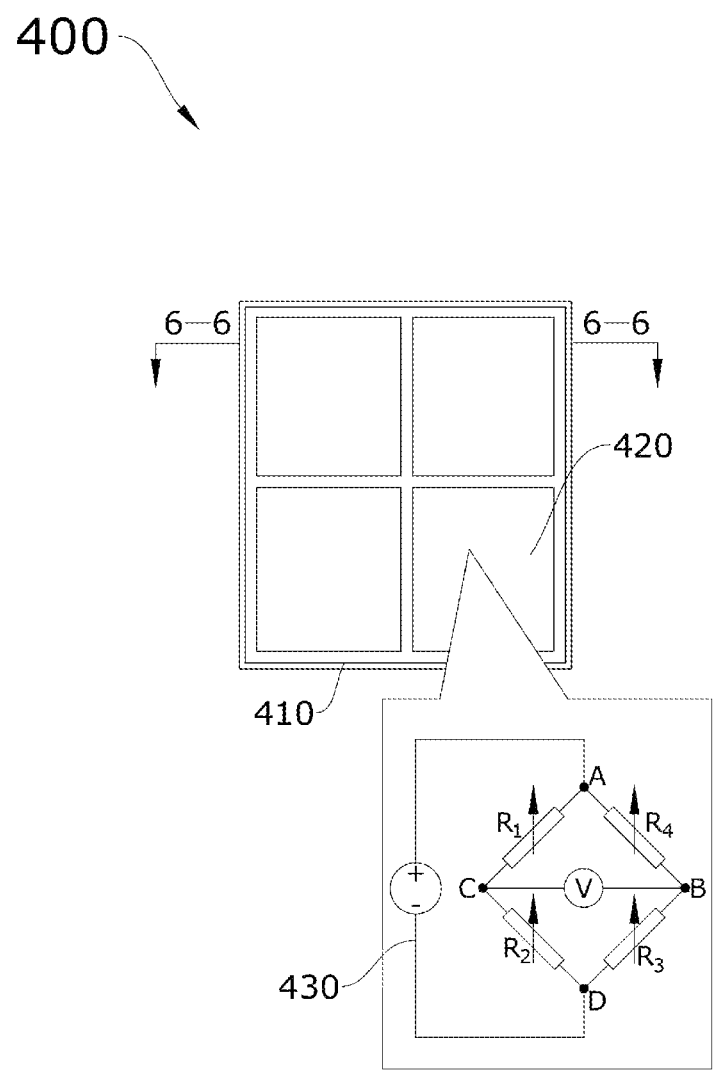

FIG. 4 conceptually illustrates a top view of a small form smart mat-scale in some embodiments.

Figure 5:
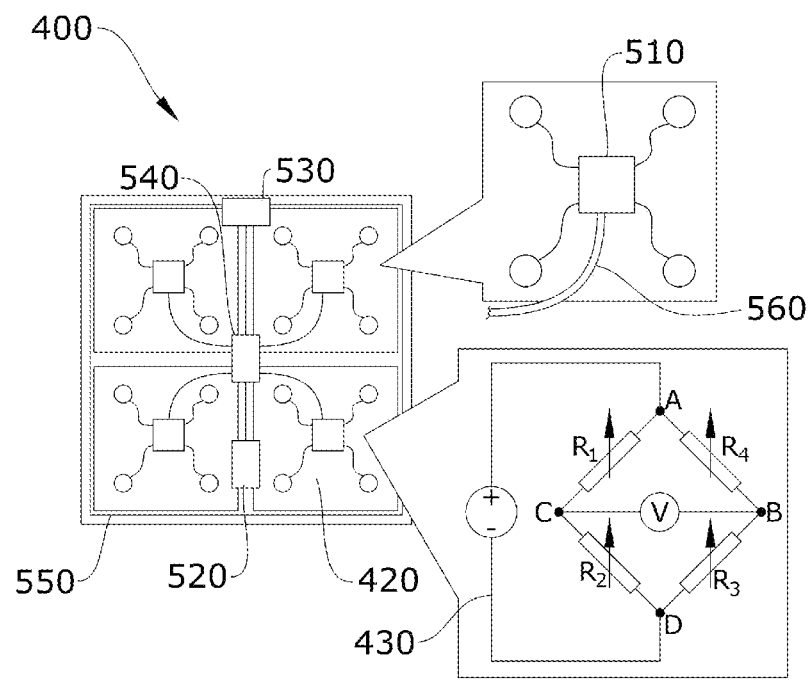

FIG. 5 conceptually illustrates a plan view of the small form smart mat-scale demonstrating embedded hardware components used for weight detection and measurement in some embodiments.

Figure 6:
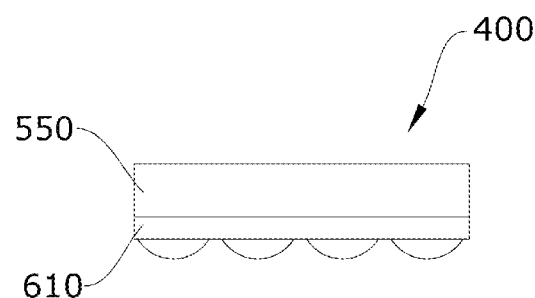

FIG. 6 conceptually illustrates a front view taken along line 6-6 of the small form smart mat-scale in FIG. 4 demonstrating a conventional textile fabric platform that is a used primarily for cleaning feet.

Figure 7:
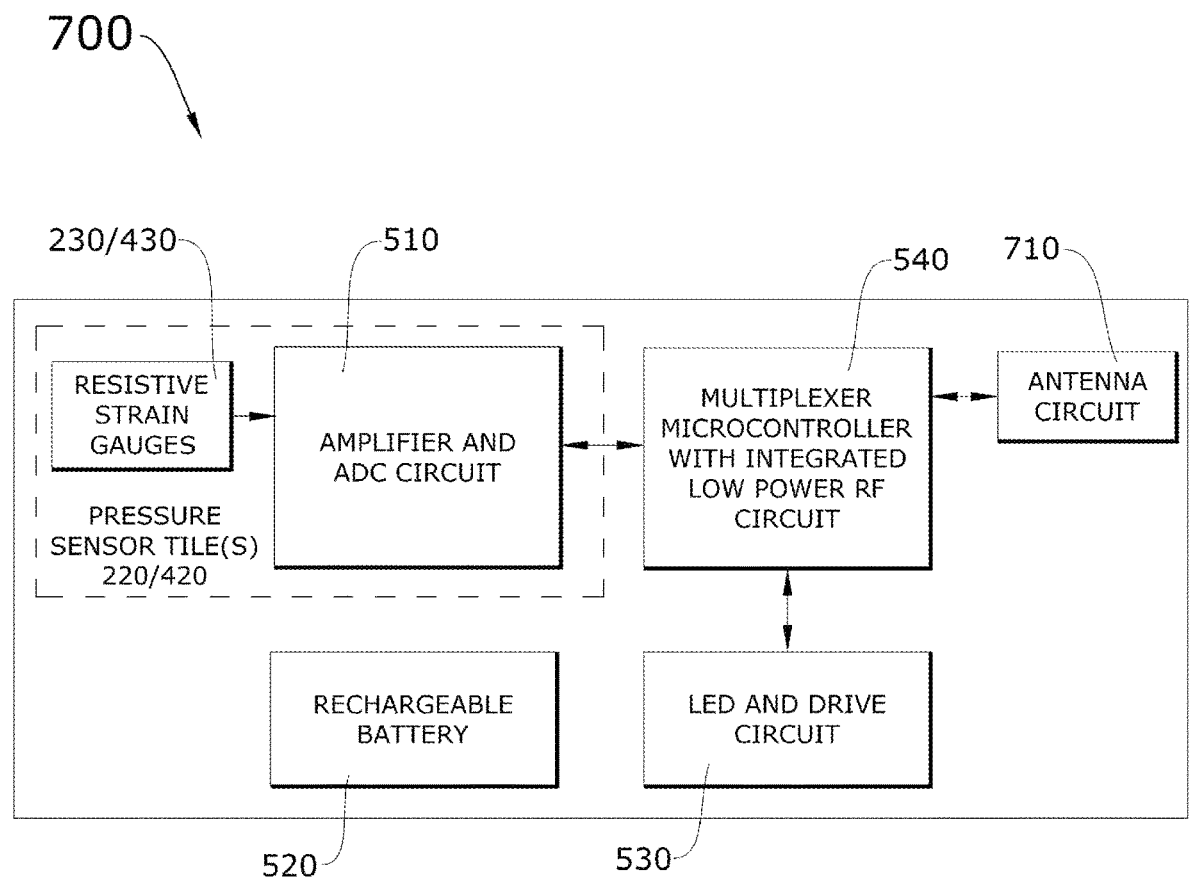

FIG. 7 conceptually illustrates a block diagram of embedded control circuitry components in some embodiments of the smart mat-scale and the small form smart mat-scale.

Figure 8:
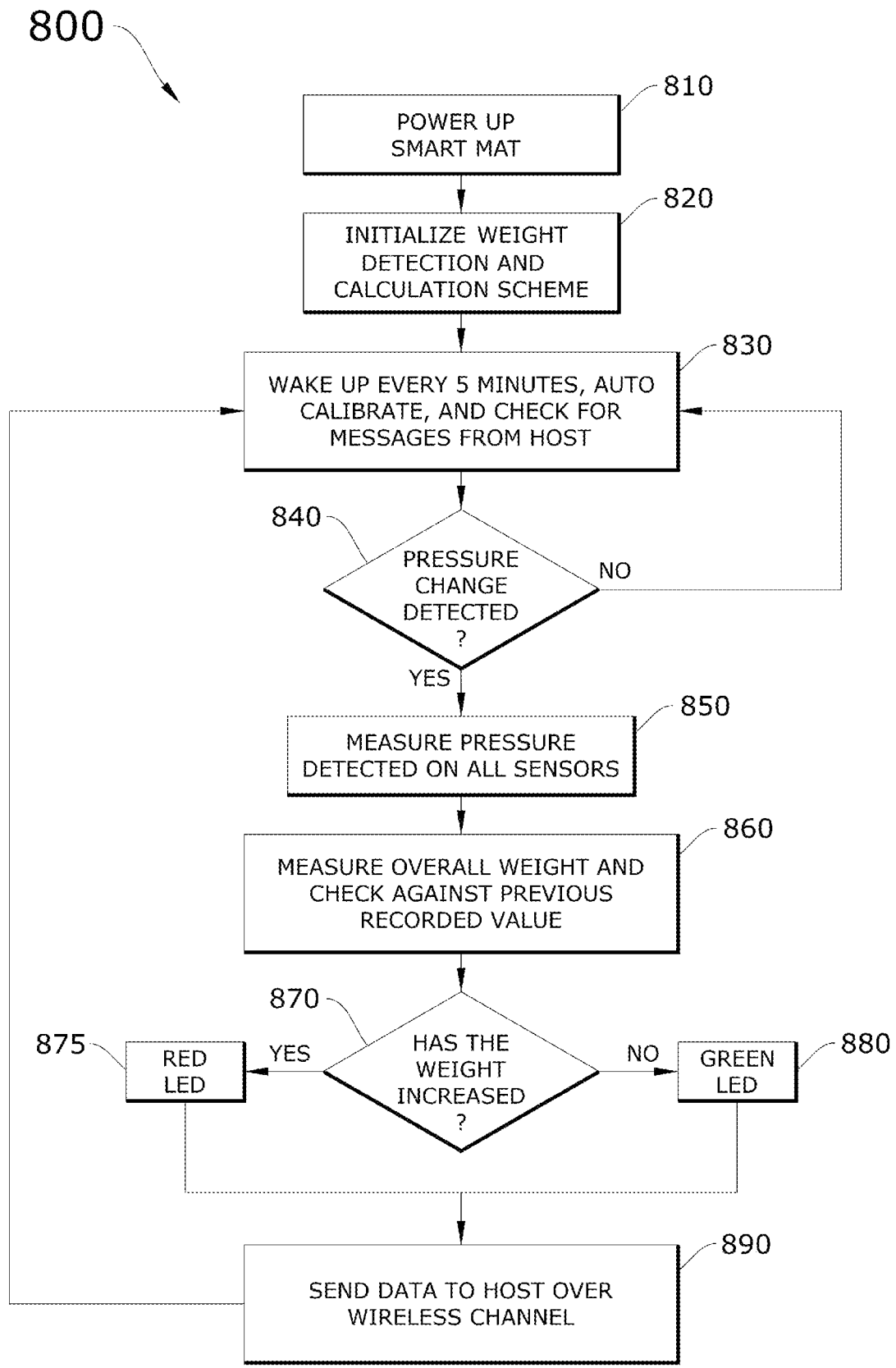

FIG. 8 conceptually illustrates a process for detecting pressure changes, measuring weight, and wirelessly communicating weight measurement data to a host in some embodiments.

Figure 9:
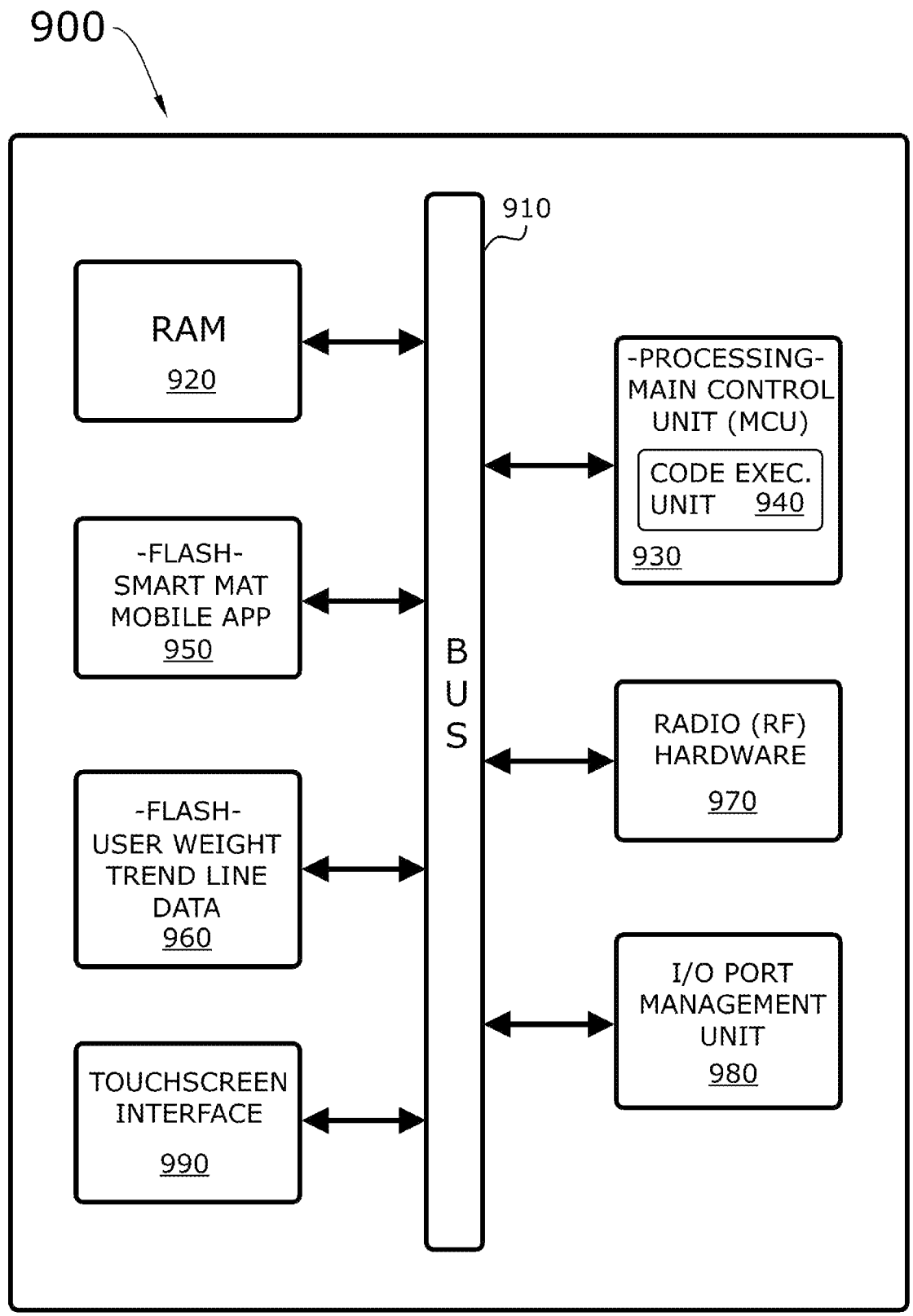

FIG. 9 conceptually illustrates a block diagram of a mobile device in some embodiments.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications.

Some embodiments of a smart mat-scale are provided to detect, measure, and communicate body weight of a user and other related data based on regular household routines (e.g., bathroom or shower routines) or other common activities (e.g., standing at a worksite with a mat in place, entering a house and wiping feet on an entryway mat) of the user. In some embodiments, the smart mat-scale is used in connection with one or more other devices in a smart mat weight detection, calculation, and communication system that is configured to wirelessly communicate weight and other related data to a mobile device, a local hub, and a gateway to externally transmit data over a network to a cloud application service and cloud database.

In a preferred embodiment, the smart mat-scale is a household mat that is made of a flexible and light weight material which is able to withstand conventional cleaning practices. In some embodiments, the smart mat-scale comprises embedded hardware components and control circuitry to automatically and inconspicuously sense body weight and related data. In some embodiments, the smart mat-scale detects and measures body weight upon sensing a change in pressure and transmits the body weight data to data processing and storage devices, such as nearby and cloud-based devices and databases, for each instance of the user applying pressure to the smart mat-scale (by stepping on, standing on, etc.) after the smart mat-scale detects and measures the body weight of the user. In some embodiments, the smart mat-scale detects and measures body weight automatically and inconspicuously communicates the body weight measurement data for review and storage, transmitting the data wirelessly to the data processing and storage devices, including at least a mobile device, such as a smartphone, of the user, a home-based data hub, and, when so configured, to a cloud application service for persistent storage in a cloud database. In this way, a user of the smart mat-scale may unconsciously step on the smart mat-scale during routine, day-to-day activities, such as washing hands at a sink, taking a shower, entering a home or building, etc. In some embodiments, the smartphone mobile device includes a mobile app and the home-based data hub includes an application for aggregating the routine, day-to-day body weight data for reporting and tracking body weight data trends of the user over time.

Embodiments of the smart mat-scale described in this specification solve the problems noted above by incorporating technology into a well-known household product-a common household mat such as a bathroom mat, a shower mat, a kitchen mat, a work area mat, a house or building entryway mat, and so on—and thereby providing a way to gather body weight data inconspicuously and automatically over time. In some embodiments, the smart mat-scale can be made of any commonly used material without impeding the reliability of body weight measurement. The transmission of data is triggered when a pressure change is detected. For example, pressure on the smart mat-scale increases when the user steps onto the smart mat-scale. Then the smart mat-scale measures the weight of the user, gathering the measured weight data for transmission to and processing by the smartphone mobile device of the user, processing at a home-based hub, or external processing on a remote cloud server (such as a cloud server hosting the cloud application service and which may be communicably connected to the cloud database). In some embodiments, the data communication is two-way, such that the processed data may also be sent from the mobile device smartphone or data hub to the smart mat-scale. In some embodiments, a visual indicator device may be embedded in the smart mat-scale which illuminates a certain color depending on a status of a current weight reading in comparison with a previous day or a consistent/inconsistent with trend data over a certain time period. For instance, the smart mat-scale may embed an LED driver with a visible LED lighting up as red for an increase in weight of the user compared to a weight trend line for the user or, alternatively, lighting up as green for a decrease or no increase in weight compared to the weight trend line.

In some embodiments, the smart mat-scale includes multiple tile shaped force sensors which detect and capture force exerted by the act of the user stepping on the smart mat-scale. In some embodiments, each force sensor is one of resistive (load cell), piezo capacitive, and another type of force measuring sensor. In some embodiments, the smart mat-scale is composed of many small tiles, allowing it to be flexible. Sensor data gathered from individual tiles of the smart mat-scale is post-processed to estimate human body weight. Based on historical data gathered from the prior usage of the smart mat-scale, the remote cloud server, via the cloud application service, or home-based hub can estimate a size of each foot of the user, pressure points of the user's feet, and other potential defects of the user's feet related to the field of pedobarography.

By way of example, FIG. 1 conceptually illustrates a smart mat weight detection, calculation, and communication system 100 that is configured to wirelessly communicate with nearby devices and over a network to a cloud application service and cloud database. As shown in this figure, the smart mat weight detection, calculation, and communication system 100 comprises a smart mat-scale 110, a cloud application service and associated cloud database 120, a mobile device 130, and a gateway and data hub 140. The smart mat-scale 110 is an electrical device that is battery powered. The smart mat-scale 110 comprises a plurality of pressure sensors, embedded control circuitry, and a battery. When powered up (or turned on), the smart mat-scale 110 monitors pressure of a top surface of the mat to detect any changes in pressure to the smart mat-scale 110. The act of a user stepping on the smart mat-scale 110 triggers the embedded control circuitry to measure pressure on all pressure sensors. The smart mat-scale 110 calculates body weight and then sends the body weight data to the mobile device 130 and/or the gateway and data hub 140. When transmitted to the gateway and data hub 140, the body weight data may be stored locally by the data hub with the data hub also processing the body weight data for transmission to the cloud application service and associated cloud database 140 to be persistently stored, when so configured. The body weight data is transmitted wirelessly by any of several supported low power RF wireless technologies like Bluetooth Low Energy (BLE), Zigbee, Z-wave, WiFi or any other proprietary wireless protocol. The mobile device 130 may also have a mobile app installed and running on a mobile processing unit of the mobile device 130. In some embodiments, either or both of the mobile device 130 (with mobile app running) and the gateway and data hub 140 may transfer the body weight data to the remote cloud server in connection with the cloud application service and associated cloud database 120, for persistent data storage and further analysis by the remote cloud server, including analysis of weight changes to identify weight fluctuations or trends (hereinafter referred to a user's weight trend line), changes in pressure points, and any other changes, fluctuations, deviations, or aberrations of data related to the field of pedobarography.

In some embodiments, the user weight data and user weight trend line data is stored in encrypted format. That is, before storing the user weight data and/or the user weight trend line data in the cloud database 120, the mobile app running on the user's mobile device smartphone, the remote cloud server or the cloud application service 120 encrypts the data by way of an encryption protocol program (or code) that implements a highly secure encryption standard. Examples of highly secure encryption standards include, without limitation, SHA256, SHA512, SHA-3, etc.

Turning to another example, FIG. 2 conceptually illustrates a top view of a smart mat-scale 200. In this figure, a structural layout of the smart mat-scale 200 is demonstrated. The smart mat-scale 200 shown in this figure comprises a mat base 210, a plurality of pressure sensor tiles 220, and a resistive strain gauge circuit 230 (also "Wheatstone bridge 230") embedded within each pressure sensor tile 220. Each of the pressure sensor tiles 220 is powered by a battery (not shown) and changes in resistance caused by the user exerting foot pressure is measured by the Wheatstone bridge 230. Nevertheless, the smart mat-scale 200 is not limited to measuring pressure by only the Wheatstone bridge 230, but instead is capable of measuring pressure by any of several other ways to measure pressure. Persons of ordinary skill in the relevant art will recognize there are many other equivalent means to measure pressure like using piezo-capacitive sensors or force restoration techniques.

In this case, the smart mat-scale 200 calculates body weight (W) as an aggregate sum of the product of individual pressure-areas, given by:

$$W = \sum_{x=0}^{n} k \cdot P_x \cdot A_x$$

In the equation above, 'k' is the co-efficient calculated during periodic automatic calibration (or "auto calibration") of the smart mat-scale 200. Auto calibration is performed at power up and periodically (e.g., every five minutes) to check pressure measured by the resistive strain gauges 230 of all pressure sensor tiles 220.

By way of another example, FIG. 3 conceptually illustrates a front view taken along line 3-3 of the smart mat-scale 200 in FIG. 2 demonstrating a conventional textile fabric platform that is a used primarily for cleaning feet. Specifically, the smart-mat scale 200 comprises a sensor control sheet 310 and a platform made of a conventional textile fabric 320. The conventional textile fabric 320 is used for the primary purpose of cleaning the user's feet. While not necessary, the conventional textile fabric platform 320 may be detached from the sensor control sheet 310.

In some embodiments, the smart mat-scale is a small form smart mat-scale that utilizes a distributed weighing scheme and is configured for daily use as a smart scale to measure body weight of a user. The small form smart mat-scale of some embodiments comprises a small subset of Wheatstone bridge circuits, each having strain gauge circuitry. In some embodiments, the strain gauge circuitry of the small subset of Wheatstone bridge circuits are placed adjacent to each other, resulting in a lighter weighing and less thick platform than conventional weighing scales.

For example, conventional weighing scales typically include four strain gauges in a Wheatstone bridge configuration with a heavy glass platform to hold body weight. The distance between the two gauges determines thickness of glass. By contrast, the small form smart mat-scale of some embodiments utilizes a plurality of Wheatstone bridge circuits, each with its own set of strain gauge circuitry. As a result, the weight and thickness of a glass platform can be reduced to less than half of the weight and thickness of the heavy glass platforms of conventional weighing scales.

In addition to measuring body weight, the small form smart mat-scale further comprises additional circuitry that is configured to measure body mass index (BMI) using bio-electrical impedance analysis and heart rate measurement in connection with the user's mobile device smartphone or the data hub.

In some embodiments, the small form smart mat-scale is configured to measure weight spread between heel and toe in a normal standing posture. In some embodiments, the small form smart mat-scale is further configured to allow for measurement of other useful data, such as weight imbalances between different feet in user's personal standing posture. The weight spread data and weight imbalances could be used to determine gait issues such as bad posture or structural deficiencies in the feet. In some embodiments, the small form smart mat-scale is configured to also measure transfer of weight from one foot to another, such as may occur while training to improve a user's golf swing or baseball bat swing.

In some embodiments, the small form smart mat-scale comprises a single slab platform that encompasses all four pressure sensor tiles and the corresponding four embedded Wheatstone bridge circuits. In some embodiments, the small form smart mat-scale comprises a plurality of foldable platform slabs which allows the small form smart mat-scale to be folded and unfolded for use as a foldable smart scale.

In some embodiments, the plurality of foldable platform slabs comprises two foldable platform slabs. In some embodiments, the plurality of foldable platform slabs comprises four foldable platform slabs.

Also, conventional weighing scales are typically made of tempered glass. Most modern scales include additional circuitry to measure body mass index (BMI) which requires placement of four conductive electrodes. Current schemes for these modern scales utilize four metal plates embossed on the glass or use of conductive oxide layer, like Indium dioxide. By contrast, each plate of the small form smart mat-scale can be made of conductive material, like carbon fiber, thereby alleviating the need for alternate materials embossed on a single glass platform.

Now turning to an embodiment of a small form smart mat-scale, FIG. 4 conceptually illustrates a top view of a small form smart mat-scale 400. As shown in this figure, the small form smart mat-scale 400 has a structural layout similar to the smart mat-scale 200, described above by reference to FIG. 2, but has a smaller 'footprint' or reduced square footage (area) than the smart mat-scale 200. In particular, the small form smart mat-scale 400 comprises a small form mat base 410 (or platform), a plurality of small form pressure sensor tiles 420 (or "weight sensing circuits 420"), and a resistive strain gauge circuit 430 ("Wheatstone bridge circuit") embedded within each small form pressure sensor tile 420. Notably, the resistive strain gauge circuit 430 (or "Wheatstone bridge circuit") shows four active resistive strain gauges, as compared to only two resistive strain gauges shown as activated in the resistive strain gauge circuit 230 described above by reference to FIG. 2. However, the number of active resistive strain gauges is a design choice that improves accuracy of readings with a greater number of active resistive strain gauges. Thus, while this example demonstrates that four strain gauges are activated for the resistive strain gauge circuit 430, the small form smart mat-scale 400 in some other embodiments can include a resistive strain gauge circuit 430 with only two active two strain gauges or another number of active strain gauges. Nevertheless it is worth nothing that the greater the number of active resistive strain gauges, the greater the accuracy of measurement that can be achieved. In this way, a greater number of activated strain gauges means that additional pressure detection is possible, such as to measurements of gait or other foot-based data.

Also, each of the small form pressure sensor tiles 420 is powered by a battery (not shown) and changes in resistance caused by the user exerting foot pressure is measured by the alternate resistive strain gauge circuit 430. Similar to the smart mat-scale 200 described above by reference to FIG. 2, the small form smart mat-scale 400 is not limited to measuring pressure by the alternate resistive strain gauge circuit 430, but is capable of measuring pressure by any of several other ways to measure pressure (e.g., piezo-capacitive sensors, force restoration techniques, etc.). Furthermore, like the smart mat-scale 200 described above by reference to FIG. 2, the small form smart mat-scale 400 calculates body weight (W) as an aggregate sum of the product of individual pressure-areas, with the equation noted above.

Now referring to another view of the small form smart mat-scale 400, FIG. 5 conceptually illustrates a plan view of the small form smart mat-scale 400. In this figure, embedded hardware components and control circuitry used for weight detection and measurement are demonstrated. Specifically, the embedded hardware components and control circuitry comprise an amplifier and analog-to-digital converter ("ADC") circuit 510, a battery 520, an LED and driver 530, a micro-controller with multiplexer and low power RF circuit 540, an alternate conventional textile fabric platform 550, and an I2C cable 560. The small form smart mat-scale 400 embeds the amplifier and ADC circuit 510 and the I2C cable 560 within each small form pressure sensor tile 420 along with the alternate resistive strain gauge circuit 430. When the alternate resistive strain gauge circuit 430 measures weight the analog weight measurement is converted into digital data by the amplifier and ADC circuit 510. In total, four amplifier and ADC circuits 510 are embedded within the small form smart mat-scale 400 and four I2C cables 560 connected to the amplifier and ADC circuits 510 transmit the digital data, converted from the analog weight measurement of the alternate resistive strain gauge circuit 430, to the micro-controller with multiplexer and low power RF circuit 540 for processing. The battery 520 provides power and may be a rechargeable battery 520. The LED and driver 530 illuminate different colors based on weight trend line details corresponding to a weight measurement history of the user. For example, the LED and driver 530 may illuminate a red light when the measured weight of the user is an increase over prior weight measurements of the user's weight trend line. The LED and driver 530 may alternately illuminate a green light when the measured weight of the user has not increased (i.e., stayed the same as previous weight measurement or decreased). The alternate conventional textile fabric platform 550 may be used as a surface for cleaning or wiping feet, thereby demonstrating that the small form smart mat-scale 400, like the smart mat-scale 200 described above by reference to FIG. 2, may be inconspicuously used as a body weight measurement device while appearing like an ordinary household mat. On the other hand, the alternate conventional textile fabric platform 550 may be used by a human to stand on and calculate/measure weight and other bodily data (e.g., BMI, heart rate, gait, center of gravity/balance, etc.). In this way, the small form smart mat-scale 400 would be acting as a smart scale, conventionally understood to be utilized for that purpose. As such, the platform material may be something more suitable for daily use as a smart weighing scale, such as an antimicrobial material, etc.

By way of another view, FIG. 6 conceptually illustrates a front view taken along line 6-6 of the small form smart mat-scale 400 in FIG. 4 demonstrating the alternate conventional textile fabric platform 550 of the small form smart mat-scale 400, which could be inconspicuous enough to pass for daily use of cleaning feet, or may be explicitly and widely known to be deployed as a smart scale and, therefore, not intended for cleaning feet. Also, an alternate sensor control sheet 610 is part of the of the small form smart mat-scale 400, placed immediately under and in contact with the alternate conventional textile fabric platform 550 at the top surface. However, the construction of the small form smart mat-scale 400 ensures that the alternate conventional textile fabric platform 550 can be detached from the alternate sensor control sheet 610 and, like the upper surface conventional textile fabric platform 320 of the smart mat-scale 200 described above by reference to FIGS. 2 and 3, replaced with another platform made of a different material or fabric. This enhances the small form smart mat-scale (and, similarly, to the smart mat-scale), since the user can replace an old, worn out textile fabric platform with a new or different platform and continue to utilize the functional aspects of the smart mat-scale (and all its internal hardware components and control circuitry).

By way of example, FIG. 7 conceptually illustrates an internal block diagram of the embedded hardware components and control circuitry of a smart mat-scale, such as the smart mat-scale 200 and the small form smart mat-scale 400, both described above by reference to FIGS. 2-6. As shown in this figure, the output voltage on the order of millivolts is generated by the resistive strain gauges 230/430 resulting from a change in pressure to the pressure sensor tiles 220/420 underneath which the resistive strain gauges 230/430 reside. The amplifier and ADC circuit 510 is used to scale up the measurement and reject noise, thereby providing a clear digital data measurement. Conventional weight scales typically include a single resistive strain gauge bridge (referred to as a "Wheatstone bridge") that feeds into an amplifier and ADC circuit. By contrast, embodiments of the smart mat-scale comprise a plurality of resistive strain gauge bridge circuits 230/430 that measure weight and, after amplification and elimination of noise by the amplifier and ADC circuit 510, are fed over I2C cables (or other suitable data transmission cables with other bus configurations/specifications) as digital weight data to the micro-controller with multiplexer and low power RF circuit 540 for processing first by the digital multiplexer. The digital multiplexer is configured to gather readings at a rate typically greater than 100 Hz so that a net instantaneous weight measurement may be obtained based on digital weight data provided by a plurality of amplifier and ADC circuits 510. Since different structural arrangements of the smart mat-scale are supported (beyond the two exemplary structural arrangements demonstrated in FIGS. 2 and 4), it is possible to have any number of amplifier and ADC circuits 510 given that the smart mat-scale provides for one amplifier and ADC circuit 510 for each pressure sensor tile 220/420.

Also, it is normal and expected that there is constant change in a user's center of gravity when the user stands on a weight scale while gathering weight, especially when the user is not perfectly still. Hence, the speed of multiplexing output of resistive strain gauge bridge data is critical to accuracy of net weight calculation. The output of the digital multiplexer is passed, as a value, to the micro-controller component of the micro-controller with multiplexer and low power RF circuit 540, which stores the digital weight data value and calculates body weight. For instant feedback to the user, the smart mat-scale checks the measured value against a most recently stored value (i.e., the last recorded value) and turns on the LED and drive circuit 530 which is configured to display different color light sources depending on the measured value. For instance, when the measured value is less than or equal to the last recorded value, a green light source indicator is shown. On the other hand, when the measured value is greater than the last recorded value, a red light source indicator is turned on by the LED and drive circuit 530. All of the embedded hardware components and control circuitry of the smart mat-scale are powered by the battery 520, which, as an embedded component in its own right, is typically a rechargeable battery 520. Also, the micro-controller with multiplexer and low power RF circuit 540 may immediately send data by way of an antenna circuit 710 to the user's mobile device smartphone, a local data hub, and/or a network gateway for transmission to an external cloud application service and corresponding cloud database. At times the user's mobile device smartphone, the local data hub, and/or the network gateway may not be in the vicinity of the smart mat-scale or may be unavailable. Hence, the micro-controller with multiplexer and low power RF circuit 540 is responsible for periodically pinging its host (mobile device smartphone, data hub, gateway) and sending data at the next available opportunity.

Turning to a flow diagram example, FIG. 8 conceptually illustrates a smart mat-scale process for detecting pressure changes, measuring weight, and wirelessly communicating weight measurement data to a host 800. As shown in this figure, the smart mat-scale process for detecting pressure changes, measuring weight, and wirelessly communicating weight measurement data to a host 800 starts at power up of the smart mat-scale (at 810). The smart mat-scale process for detecting pressure changes, measuring weight, and wirelessly communicating weight measurement data to a host 800 then initializes a weight detection and calculation scheme (at 820) which triggers automatic and periodic wake up (e.g., every five minutes or other configurable period), auto calibration (which happens at power up, as well as periodically in some embodiments), and checking for messages from the host (at 830), where the host is one of the user's mobile device or smartphone, the local data hub, or the gateway. A moving average of non-external triggered weight readings is used to auto calibrate and set the "zero" value. When checking for any pending messages from the host, the smart mat-scale process for detecting pressure changes, measuring weight, and wirelessly communicating weight measurement data to a host 800 also scans pressure readings of all sensors.

Next, the smart mat-scale process for detecting pressure changes, measuring weight, and wirelessly communicating weight measurement data to a host 800 determines (at 840) whether there is a change in pressure detected. When no change in pressure is detected, the smart mat-scale process for detecting pressure changes, measuring weight, and wirelessly communicating weight measurement data to a host 800 returns to the step for automatic wake up, calibration, and message checking (at 830) and waits for the wake up period to then check pressure again. In some embodiments, the micro-controller actively scans for changes in pressure and wakes up via an interrupt. When a change in pressure is affirmatively detected, the smart mat-scale process for detecting pressure changes, measuring weight, and wirelessly communicating weight measurement data to a host 800 measures pressure detected on all pressure sensor tiles (at 850). In some embodiments, the smart mat-scale process for detecting pressure changes, measuring weight, and wirelessly communicating weight measurement data to a host 800 stores the values from all sensors in non-volatile memory before calculating the user's body weight. Thus, in the next step the smart mat-scale process for detecting pressure changes, measuring weight, and wirelessly communicating weight measurement data to a host 800 calculates or measures overall weight and checks the weight against previous recorded weight (at 860). In checking the previous weight, the smart mat-scale process for detecting pressure changes, measuring weight, and wirelessly communicating weight measurement data to a host 800 compares it to the current overall measured weight and determines (at 870) whether the weight of the user has increased. When the weight of the user has increased, the smart mat-scale process for detecting pressure changes, measuring weight, and wirelessly communicating weight measurement data to a host 800 illuminates the LED red (at 875) and continues to the next step of sending the overall weight measurement data to the host over the wireless channel (at 890). On the other hand, when the weight of the user has not increased, the smart mat-scale process for detecting pressure changes, measuring weight, and wirelessly communicating weight measurement data to a host 800 illuminates the LED green (at 880) and continues to the next step of sending the overall weight measurement data to the host over the wireless channel (at 890). The wireless channel wireless channel is one of those noted above, such Zigbee, BLE, WiFi, Z-wave, or another wireless data protocol. After sending the current overall weight measurement data to the host, the smart mat-scale process for detecting pressure changes, measuring weight, and wirelessly communicating weight measurement data to a host 800 returns back to the step for automatic wake up, calibration, and message checking (at 830) and waits for the wake up period to then check pressure again.

The smart mat-scale process for detecting pressure changes, measuring weight, and wirelessly communicating weight measurement data to a host 800 continues in this loop until the power of the smart mat-scale is shut down. This continuous looping of the smart mat-scale process for detecting pressure changes, measuring weight, and wirelessly communicating weight measurement data to a host 800 involves the micro-controller trying to establish a connection with a mobile device smartphone or the gateway and synchronizing any new data or configuration settings. However, after the smart mat-scale process for detecting pressure changes, measuring weight, and wirelessly communicating weight measurement data to a host 800 proceeds checks quiescent sensor readings, the smart mat-scale is configured to conserve battery power by going to sleep to conserve battery power.

Although the smart mat-scale and small form smart mat-scale described above include pressure sensor tiles of no particular size, it is noted that typically the pressure sensor tiles would be sized to be suitable for measuring weight of a human user by the pressure exerted by the feet of the human user, while also limiting the size of each pressure sensor tile so as to allow the smart mat-scale to be somewhat flexible (as opposed to being a rigid smart mat-scale). In other embodiments, the pressure sensor tiles could be made much smaller, thereby allowing much finer measurement of pressure exerted by the human user's feet. For example, such a finer/smaller construction allows finer detection of changes in pressure patterns between left and right foot, and may be useful in detecting other data points, such as gait or center of gravity imbalances.

Regardless of the size of the pressure sensor tiles, it is possible that the smart mat-scale could detect and measure weight of non-human subjects, such as house pets (e.g. a family dog or cat). Indeed, the smart mat-scale could even be deployed for routine use in measuring weight of a non-human subject (animal) by, for example, detaching the conventional textile fabric platform 320 from the sensor control sheet 310 of the smart mat-scale 200, described above by reference to FIGS. 2 and 3, or detaching the alternate conventional textile fabric platform 550 from the alternate sensor control sheet 610, described above by reference to FIGS. 4-6, and replacing the detached platform with a different platform made of different fabric or material that encourages the non-human subject (animal) to approach, step onto, and stand on the platform of the smart mat-scale and/or small form smart mat-scale. For example, a scent that attracts an animal to the smart mat-scale and/or small form smart mat-scale. Similarly, one could detach the fabric platform and replace with a different textile fabric platform that would discourage the non-human subject (animal) from stepping onto, standing on, sitting on, or laying on the smart mat-scale and/or small form smart mat-scale. For example, a scent the repels an animal away from the smart mat-scale and/or small form smart mat-scale or a textured fabric platform that is not comfortable to an animal but is suitable for human feet.

Other materials for the platform may be used in place of conventional textile fabric platform or other platform surface fabric. For example, anti-microbial materials or coatings, could be attached to the top surface of the platform. In some embodiments, the platform as a whole can be made of any material as long as application of weight does not cause deformation large enough to cause the platform to touch the floor. Alternate materials include, without limitation, wood, tempered glass, solid plastic, carbon fiber, rubber, neoprene, textile, metal, or any combination of these other materials. In some embodiments, the platform achieves a light weight but high strength construction quality by utilization of strong, light weighing materials or forms, such as corrugated sheets, honey comb or mesh shaped structures made of the alternate or other materials. Furthermore, the platform could also be made of an anti-microbial material or coating to promote hygiene in a common use area like gymnasiums or other shared or public spaces or facilities requiring common use of a weighing scale. Very often users stand on a weighing scale platform without footwear (bare footed) to measure metrics like body mass index (BMI), heart rate, etc. As such, anti-microbial materials or coatings would be beneficially attached to the platform to maintain the common hygiene of the public or shared space or facility.

By way of example, FIG. 9 conceptually illustrates a block diagram of a block diagram of a mobile device 900 that acts as a host to the smart mat-scale in some embodiments. In some embodiments, the mobile device 900 is a smartphone that runs a smart mat-scale mobile app used in connection with receiving weight data from the smart mat-scale and for tracking user weight trend line data. As shown in this figure, the mobile device 900 comprises a bus 910, a random access memory (RAM) 920, a main control unit (MCU) 930 for runtime processing of the mobile device 900 as a host to receive weight data from the smart mat-scale and to track user weight trend line data, a code execution unit 940 embedded within the MCU 930, a first persistent flash memory 950 that stores the smart mat-scale mobile app which is loaded into RAM 920 when launched and executed by the code execution unit 940 of the MCU 930 to receive and store the weight data and to provide an interface for the user to visualize the user weight trend line data, a second persistent flash memory 960 that stores the user trend line data, radio (RF) hardware 970 to transmit and receive wireless radio signals via Zigbee, BLE, WiFi, Z-wave, or another wireless data protocol, an input/output (I/O) management unit 980, and a touchscreen interface 990.

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

I claim:

1. A smart mat that senses body weight and transmits weight data to a host electronic device, said smart mat comprising:
    a smart mat platform comprising a first layer made of a conventional flexible textile material that is easy to clean and suitable for a user to stand upon, a second sensor control sheet layer, and hardware components and control circuitry to detect force and measure weight of the user while the user stands upon the conventional flexible textile material at the first layer of the smart mat platform, wherein the hardware components and control circuitry comprise a plurality of pressure sensors that detect and measure force applied by the two feet of the user, wherein the smart mat further comprises a plurality of tiles within which the plurality of pressure sensors are embedded into the second sensor control sheet layer of the smart mat platform, said plurality of tiles aligned in a pattern to fit within a perimeter that approximates a border of the smart mat;
    a remote cloud-based server configured to aggregate and track body weight data of the user in a cloud database;
    a smartphone of the user that is configured to receive data transmissions from the household mat and transmit the data to the remote cloud-based server for tracking and aggregation; and
    a gateway for wireless communication between the smart mat, the smartphone of the user, and the remote cloud-based server.

2. The smart mat of claim 1, wherein the plurality of pressure sensors are organized into a Wheatstone bridge circuit.

3. The smart mat of claim 2, wherein the smart mat comprises a set of four adjacently placed Wheatstone bridge circuits in a small form smart mat configuration.

4. The smart mat of claim 2, wherein the smart mat comprises a plurality of more than four adjacently placed Wheatstone bridge circuits in a standard form smart mat configuration.

5. A smart mat weight detection, calculation, and communication system configured to measure weight of a user and wirelessly transmit weight data to a host, said smart mat weight detection, calculation, and communication system comprising:
    a gateway wireless communication device;
    a smartphone mobile device of a user; and
    a smart mat comprising a platform and a plurality of adjacently placed weight sensing circuits, wherein the platform comprises a plurality of foldable slab platforms that are configured to fold the smart mat into a smaller carrying surface area and unfold the smart mat for weight sensing usage, wherein each foldable slab platform comprises a plurality of adjacently slab-placed weight sensing circuits, wherein the smart mat is configured to detect a change in pressure when the user stands on the platform, measure weight of the user while standing on the platform, and wirelessly transmit user weight data to a host via the gateway wireless communication device.

6. The smart mat weight detection, calculation, and communication system of claim 5, wherein the host comprises one of the smartphone mobile device of the user and a local data processing and storage computing device hub.

7. The smart mat weight detection, calculation, and communication system of claim 5, wherein the smart mat is further configured to measure heart rate of the user and body mass index (BMI) using bioelectrical impedance analysis as performed by the smartphone mobile device of the user.

8. The smart mat weight detection, calculation, and communication system of claim 5, wherein the platform and the plurality of foldable slab platforms are configured to be detached and replaced with a single slab platform that encompasses the plurality of adjacently placed weight sensing circuits.

9. The smart mat weight detection, calculation, and communication system of claim 5 further comprising an external cloud server and cloud database, wherein the external cloud server hosts a cloud application service that is configured to receive the user weight data via the gateway wireless communication device when the external cloud server is the host.

\* \* \* \* \*